United States Patent [19]

Sih

[11] 4,281,191
[45] Jul. 28, 1981

[54] 19-HYDROXY-19-METHYL-PG AMIDES

[75] Inventor: John C. Sih, Kalamazoo, Mich.

[73] Assignee: The Upjohn Company, Kalamazoo, Mich.

[21] Appl. No.: 133,203

[22] Filed: Mar. 24, 1980

Related U.S. Application Data

[62] Division of Ser. No. 25,878, Apr. 2, 1979, abandoned.

[51] Int. Cl.$^3$ .................... C07C 103/19; A61K 31/16
[52] U.S. Cl. .................................. 564/189; 564/169; 564/171; 424/320; 424/324
[58] Field of Search ........... 260/557 R, 559 B, 559 R; 560/10, 121; 562/427; 564/189, 169, 171

[56] References Cited

U.S. PATENT DOCUMENTS

| | | | |
|---|---|---|---|
| Re. 30,287 | 5/1980 | Marx et al. ..................... | 560/121 X |
| 3,981,868 | 9/1976 | Bernady et al. ............. | 260/557 R X |
| 4,152,527 | 5/1979 | Hess et al. ..................... | 260/557 B X |
| 4,169,895 | 10/1979 | Hess et al. ................. | 260/556 AC X |
| 4,191,694 | 3/1980 | Skuballa et al. .......... | 260/556 AC X |

FOREIGN PATENT DOCUMENTS 2505519 8/1975 Fed. Rep. of Germany ........... 560/121

OTHER PUBLICATIONS

Derwent Farmdoc CPI, No. 32921W/20, (Abstract—French 2,239,458).

Primary Examiner—Thomas A. Waltz
Attorney, Agent, or Firm—Robert A. Armitage

[57] ABSTRACT

The present invention provides novel 19-hydroxy-19-methyl-PG amides and methods for their preparation and pharmacological uses for the induction of prostaglandin-like effects.

178 Claims, No Drawings

19-HYDROXY-19-METHYL-PG AMIDES

CROSS REFERENCE TO RELATED APPLICATIONS

The present application is a division of Ser. No. 025,878, filed Apr. 2, 1979, now abandoned.

BACKGROUND OF THE INVENTION

The present invention relates to novel prostaglandin analogs. Particularly, these compounds are analogs of the prostaglandins wherein the C-19 position is substituted by hydroxy, i.e., 19-hydroxy-19-methyl-PG compounds. Most particularly, the present invention relates to novel 19-hydroxy-19-methyl-PG amides, a disclosure of the preparation and use of which is incorporated here by reference from U.S. Pat. No. 4,228,104.

PRIOR ART

Prostaglandin analogs exhibiting hydroxylation in the 19-position are known in the art. See, for example, U.S. Pat. No. 4,127,612, Sih, J. C., Prostaglandins 13:831 (1977) and U.S. Pat. Nos. 3,657,316, 3,878,046, and 3,922,297. See also the additional references cited in U.S. Ser. No. 025,878, now abandoned.

SUMMARY OF THE INVENTION

The present invention particularly provides a compound of the formula

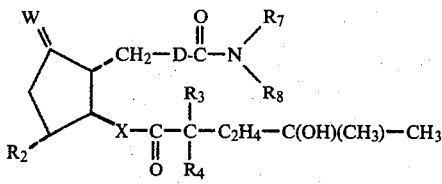

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)$_2$—O—(CH$_2$)$_2$,
(9) —CH$_2$—O—(CH$_2$)$_3$—,
(10) —(m—Ph)—(CH$_2$)$_2$—, or
(11) —(m—Ph)—O—CH$_2$—,
wherein —(m—Ph)— is inter-meta-phenylene, and wherein g is zero, one, two, or three;

wherein Q is $\alpha$-OH:$\beta$-R$_5$ or $\alpha$-R$_5$:$\beta$-OH, wherein R$_5$ is hydrogen or methyl;

wherein R$_7$ and R$_8$ are hydrogen, alkyl of one to 12 carbon atoms, inclusive, benzyl, or phenyl, being the same or different;

wherein R$_2$ is hydrogen, hydroxyl, or hydroxymethyl;

wherein R$_3$ and R$_4$ are hydrogen, methyl, or fluoro, being the same or different, with the proviso that one of R$_3$ and R$_4$ is fluoro only when the other is hydrogen or fluoro;

wherein W is oxo, methylene, $\alpha$-OH:$\beta$-H, or $\alpha$-H:$\beta$-OH; and wherein X is cis- or trans—CH=CH—, —C≡C—, or —CH$_2$CH$_2$—.

With regard to the divalent the substituents described above (e.g., Q) these divalent radicals are defined as $\alpha$-R$_i$:$\beta$-R$_j$, wherein R$_i$ represents the substituent of the divalent moiety in the alpha configuration with respect to the ring and R$_j$ represents the substituent of the divalent moiety in the beta configuration with respect to the plane of the ring. Accordingly, when Q is defined as $\alpha$-OH:$\beta$-R$_5$, the hydroxy of the Q moiety is in the alpha configuration, i.e., as in the natural prostaglandin, and the R$_5$ substituent is in the beta configuration.

Specific embodiments of the present invention include:
19-hydroxy-19-methyl-PGF$_{2\alpha}$, amide,
11-deoxy-11$\alpha$-hydroxymethyl-19-hydroxy-19-methyl-PGF$_{2\alpha}$, amide,
19-hydroxy-19-methyl-PGF$_{2\beta}$, amide,
11-deoxy-11$\alpha$-hydroxymethyl-19-hydroxy-19-methyl-PGF$_{2\beta}$, amide,
19-hydroxy-19-methyl-PGE$_2$, amide,
11-deoxy-11$\alpha$-hydroxymethyl-19-hydroxy-19-methyl-PGE$_2$, amide,
9-deoxo-9-methylene-19-hydroxy-19-methyl-PGE$_2$, amide
9-deoxo-9-methylene-11-deoxy-19-hydroxy-19-methyl-PGE$_2$, amide,
9-deoxo-9-methylene-11-deoxy-11$\alpha$-hydroxymethyl-19-hydroxy-19-methyl-PGE$_2$, amide,
4,5-didehydro-19-hydroxy-19-methyl-PGF$_{1\alpha}$, amide,
4,5-didehydro-19-hydroxy-19-methyl-15(S)-15-methyl-PGF$_{1\alpha}$, amide,
4,5,13,14-tetradehydro-19-hydroxy-19-methyl-PGF$_{1\alpha}$, amide,
4,5,13,14-tetradehydro-19-hydroxy-19-methyl-16,16-difluoro-PGF$_{1\alpha}$, amide,
4,5,13,14-tetradehydro-19-hydroxy-19-methyl-11-deoxy-PGF$_{1\alpha}$, amide,
4,5,13,14-tetradehydro-19-hydroxy-19-methyl-11-deoxy-16,16-difluoro-PGF$_{1\alpha}$, amide,
4,5-dideoxy-19-hydroxy-19-methyl-11-deoxy-11$\alpha$-hydroxymethyl-PGF$_{1\alpha}$, amide,
4,5-dideoxy-19-hydroxy-19-methyl-11-deoxy-11$\alpha$-hydroxymethyl-15(S)-15-methyl-PGF$_{1\alpha}$, amide,
4,5,13,14-tetradehydro-19-hydroxy-19-methyl-11-deoxy-11$\alpha$-hydroxymethyl-PGF$_{1\alpha}$, amide,
4,5,13,14-tetradehydro-19-hydroxy-19-methyl-11-deoxy-11$\alpha$-hydroxymethyl-16,16-difluoro-PGF$_{1\alpha}$, amide,
4,5-didehydro-19-hydroxy-19-methyl-PGF$_{1\beta}$, amide,
4,5-didehydro-19-hydroxy-19-methyl-15(S)-15-methyl-PGF$_{1\beta}$, amide,
4,5,13,14-tetradehydro-19-hydroxy-19-methyl-PGF$_{1\beta}$, amide,
4,5,13,14-tetradehydro-19-hydroxy-19-methyl-16,16-difluoro-PGF$_{1\beta}$, amide,
4,5,13,14-tetradehydro-19-hydroxy-19-methyl-11-deoxy-PGF$_{1\beta}$, amide,
4,5,13,14-tetradehydro-19-hydroxy-19-methyl-19-methyl-11-deoxy-16,16-difluoro-PGF$_{1\beta}$, amide,
4,5-didehydro-19-hydroxy-19-methyl-11-deoxy-11$\alpha$-hydroxymethyl-PGF$_{1\beta}$, amide,
4,5-didehydro-19-hydroxy-19-methyl-11-deoxy-11$\alpha$-hydroxymethyl-15(S)-15-methyl-PGF$_{1\beta}$, amide,
4,5,13,14-tetradehydro-19-hydroxy-19-methyl-11-deoxy-11$\alpha$-hydroxymethyl-PGF$_{1\beta}$, amide,
4,5,13,14-tetradehydro-19-hydroxy-19-methyl-11-deoxy-11$\alpha$-hydroxymethyl-16,16-difluoro-PGF$_{1\beta}$, amide,
4,5-didehydro-19-hydroxy-19-methyl-PGE$_1$, amide, 4,5-didehydro-19-hydroxy-19-methyl-15(S)-15-methyl-PGE$_1$, amide,
4,5,13,14-tetradehydro-19-hydroxy-19-methyl-PGE$_1$, amide,
4,5,13,14-tetradehydro-19-hydroxy-19-methyl-16,16-difluoro-PGE$_1$, amide,
4,5,13,14-tetradehydro-19-hydroxy-19-methyl-11-deoxy-PGE$_1$, amide,
4,5,13,14-tetradehydro-19-hydroxy-19-methyl-11-deoxy-16,16-difluoro-PGE$_1$, amide,
4,5-didehydro-19-hydroxy-19-methyl-11-deoxy-11α-hydroxymethyl-PGE$_1$, amide,
4,5-didehydro-19-hydroxy-19-methyl-11-deoxy-11α-hydroxymethyl-15(S)-15-methyl-PGE$_1$, amide,
4,5,13,14-tetradehydro-19-hydroxy-19-methyl-11-deoxy-11α-hydroxymethyl-PGE$_1$, amide,
4,5,13,14-tetradehydro-19-hydroxy-19-methyl-11-deoxy-11α-hydroxymethyl-16,16-difluoro-PGE$_1$, amide,
4,5-didehydro-19-hydroxy-19-methyl-9-deoxo-9-methylene-PGE$_1$, amide,
4,5-didehydro-19-hydroxy-19-methyl-9-deoxo-9-methylene-15(S)-15-methyl-PGE$_1$, amide,
4,5,13,14-tetradehydro-19-hydroxy-19-methyl-9-deoxo-9-methylene-PGE$_1$, amide,
4,5,13,14-tetradehydro-19-hydroxy-19-methyl-9-deoxo-9-methylene-16,16-difluoro-PGE$_1$, amide,
4,5,13,14-tetradehydro-19-hydroxy-19-methyl-9-deoxo-9-methylene-11-deoxy-PGE$_1$, amide,
4,5,13,14-tetradehydro-19-hydroxy-19-methyl-9-deoxo-9-methylene-11-deoxy-16,16-difluoro-PGE$_1$, amide,
4,5-didehydro-19-hydroxy-19-methyl-9-deoxo-9-methylene-11-deoxy-11α-hydroxymethyl-PGE$_1$, amide,
4,5-didehydro-19-hydroxy-19-methyl-9-deoxo-9-methylene-11-deoxy-11α-hydroxymethyl-15(S)-15-methyl-PGE$_1$, amide,
4,5,13,14-tetradehydro-19-hydroxy-19-methyl-9-deoxo-9-methylene-11-deoxy-11α-hydroxymethyl-PGE$_1$, amide,
4,5,13,14-tetradehydro-19-hydroxy-19-methyl-9-deoxo-9-methylene-11-deoxy-11α-hydroxymethyl-16,16-difluoro-PGE$_1$, amide,
2,3-didehydro-19-hydroxy-19-methyl-PGF$_1$α, amide,
2,3-didehydro-19-hydroxy-19-methyl-16,16-difluoro-PGF$_1$α, amide,
2,3-didehydro-19-hydroxy-19-methyl-15(S)-15-methyl-PGF$_1$α, amide,
2,3-didehydro-19-hydroxy-19-methyl-11-deoxy-11α-hydroxymethyl-PGF$_1$α, amide,
2,3-didehydro-19-hydroxy-19-methyl-11-deoxy-11α-hydroxymethyl-16,16-difluoro-PGF$_1$α, amide,
2,3-didehydro-19-hydroxy-19-methyl-11-deoxy-11α-hydroxymethyl-15(S)-15-methyl-PGF$_1$α, amide,
2,3-didehydro-19-hydroxy-19-methyl-PGF$_1$β, amide,
2,3-didehydro-19-hydroxy-19-methyl-16,16-difluoro-PGF$_1$β, amide,
2,3-didehydro-19-hydroxy-19-methyl-15(S)-15-methyl-PGF$_1$β, amide,
2,3-didehydro-19-hydroxy-19-methyl-11-deoxy-11α-hydroxymethyl-PGF$_1$β, amide,
2,3-didehydro-19-hydroxy-19-methyl-11-deoxy-11α-hydroxymethyl-16,16-difluoro-PGF$_1$β, amide,
2,3-didehydro-19-hydroxy-19-methyl-11-deoxy-11α-hydroxymethyl-15(S)-15-methyl-PGF$_1$β, amide,
2,3-didehydro-19-hydroxy-19-methyl-PGE$_1$, amide,
2,3-didehydro-19-hydroxy-19-methyl-16,16-difluoro-PGE$_1$, amide,
2,3-didehydro-19-hydroxy-19-methyl-15(S)-15-methyl-PGE$_1$, amide,
2,3-didehydro-19-hydroxy-19-methyl-11-deoxy-11α-hydroxymethyl-PGE$_1$, amide,
2,3-didehydro-19-hydroxy-19-methyl-11-deoxy-11α-hydroxymethyl-16,16-difluoro-PGE$_1$, amide,
2,3-didehydro-19-hydroxy-19-methyl-11-deoxy-11α-hydroxymethyl-15(S)-15-methyl-PGE$_1$, amide,
2,3-didehydro-19-hydroxy-19-methyl-9-deoxo-9-methylene-PGE$_1$, amide,
2,3-didehydro-19-hydroxy-19-methyl-9-deoxo-9-methylene-16,16-difluoro-PGE$_1$, amide,
2,3-didehydro-19-hydroxy-19-methyl-9-deoxo-9-methylene-15(S)-15-methyl-PGE$_1$, amide,
2,3-didehydro-19-hydroxy-19-methyl-9-deoxo-9-methylene-11-deoxy-11α-hydroxymethyl-PGE$_1$, amide,
2,3-didehydro-19-hydroxy-19-methyl-9-deoxo-9-methylene-11-deoxy-11α-hydroxymethyl-16,16-difluoro-PGE$_1$, amide,
2,3-didehydro-19-hydroxy-19-methyl-9-deoxo-9-methylene-11-deoxy-11α-hydroxymethyl-15(S)-15-methyl-PGE$_1$, amide,
19-hydroxy-19-methyl-PGF$_1$α, amide,
16,16-dimethyl-19-hydroxy-19-methyl-PGF$_1$α, amide,
16,16-difluoro-19-hydroxy-19-methyl-PGF$_1$α, amide,
13,14-dihydro-19-hydroxy-19-methyl-PGF$_1$α, amide,
11-deoxy-11α-hydroxymethyl-19-hydroxy-19-methyl-PGF$_1$α, amide,
11-deoxy-11α-hydroxymethyl-16,16-dimethyl-19-hydroxy-19-methyl-PGF$_1$α, amide,
11-deoxy-11α-hydroxymethyl-16,16-difluoro-19-hydroxy-19-methyl-PGF$_1$α, amide,
11-deoxy-11α-hydroxymethyl-13,14-dihydro-19-hydroxy-19-methyl-PGF$_1$α, amide,
19-hydroxy-19-methyl-PGF$_1$β, amide,
16,16-dimethyl-19-hydroxy-19-methyl-PGF$_1$β, amide,
16,16-difluoro-19-hydroxy-19-methyl-PGF$_1$β, amide,
13,14-dihydro-19-hydroxy-19-methyl-PGF$_2$β, amide,
19-hydroxy-19-methyl-PGE$_1$, amide,
16,16-dimethyl-19-hydroxy-19-methyl-PGE$_1$, amide,
16,16-difluoro-19-hydroxy-19-methyl-PGE$_1$, amide,
13,14-dihydro-19-hydroxy-19-methyl-PGE$_1$, amide,
11-deoxy-11α-hydroxymethyl-19-hydroxy-19-methyl-PGE$_1$, amide,
11-deoxy-11α-hydroxymethyl-16,16-dimethyl-19-hydroxy-19-methyl-PGE$_1$, amide,
11-deoxy-11α-hydroxymethyl-16,16-difluoro-19-hydroxy-19-methyl-PGE$_1$, amide,
11-deoxy-11α-hydroxymethyl-13,14-dihydro-19-hydroxy-19-methyl-PGE$_1$, amide,
9-deoxo-9-methylene-19-hydroxy-19-methyl-PGE$_1$, amide,
9-deoxo-9-methylene-16,16-dimethyl-19-hydroxy-19-methyl-PGE$_1$, amide,
9-deoxo-9-methylene-16,16-difluoro-19-hydroxy-19-methyl-PGE$_1$, amide,
9-deoxo-9-methylene-13,14-dihydro-19-hydroxy-19-methyl-PGE$_1$, amide,
9-deoxo-9-methylene-11-deoxy-11α-hydroxymethyl-19-hydroxy-19-methyl-PGE$_1$, amide,
9-deoxo-9-methylene-11-deoxy-11α-hydroxymethyl-16,16-dimethyl-19-hydroxy-19-methyl-PGE$_1$, amide, 9-deoxo-9-methylene-11-deoxy-11α-hydroxymethyl-16,16-difluoro-19-hydroxy-19-methyl-PGE$_1$, amide, and 9-deoxo-9-methylene-11-deoxy-11α-hydroxymethyl-13,14-dihydro-19-hydroxy-19-methyl-PGE$_1$, amide.

The compounds of the present invention are particularly useful for inducing prostaglandin-like biological effects, as is described in U.S. Ser. No. 025,878, now abandoned. Uses of compounds in accordance with the present invention include, therefore, anti-asthmatic indications.

I claim:

1. A compound of the formula

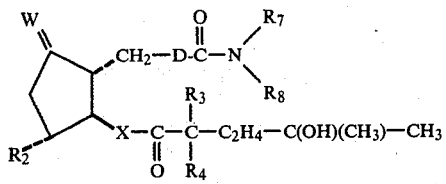

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
(5) —(CH$_2$)$_3$—(CH$_2$)$_g$—CH$_2$—,
(6) —(CH$_2$)$_3$—CH$_2$—CF$_2$—,
(7) —(CH$_2$)$_3$—O—CH$_2$—,
(8) —(CH$_2$)$_2$—O—(CH$_2$)$_2$,
(9) —CH$_2$—O—(CH$_2$)$_3$—,
(10) —(m—Ph)—(CH$_2$)$_2$—, or
(11) —(m—Ph)—O—CH$_2$—, wherein —(m—Ph)— is inter-meta-phenylene, and wherein g is zero, one, two, or three;
wherein Q is α-OH:β-R$_5$ or α-R$_5$: β-OH, wherein R$_5$ is hydrogen or methyl;
wherein R$_7$ and R$_8$ are hydrogen, alkyl of one to 12 carbon atoms, inclusive, benzyl, or phenyl, being the same or different;
wherein R$_2$ is, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is oxo, methylene, α-OH:β-H, or α-H:β-OH; and
wherein X is cis- or trans—CH=CH—, —C≡C—, or —CH$_2$CH$_2$—.

2. A compound according to claim 1, wherein g is one or three.

3. A compound according to claim 2, wherein D is cis—CH=CH—CH$_2$—(CH$_2$)$_g$—CH$_2$—.

4. A compound according to claim 3, wherein W is α-OH:β-H.

5. A compound according to claim 4, wherein R$_2$ is hydroxyl and X is trans—CH=CH—.

6. 19-hydroxy-19-methyl-PGF$_2$α, amide, a compound according to claim 5.

7. A compound according to claim 4, wherein R$_2$ is hydroxymethyl and X is trans—CH=CH—.

8. 11-deoxy-11α-hydroxymethyl-19-hydroxy-19-methyl-PGF$_2$α, amide, a compound, according to claim 7.

9. A compound according to claim 3, wherein W is β-OH:α-H.

10. A compound to claim 9, wherein R$_2$ is hydroxyl and X is trans—CH=CH—.

11. 19-hydroxy-19-methyl-PGF$_2$β, amide, a compound according to claim 10.

12. A compound according to claim 9, wherein R$_2$ is hydroxymethyl and X is trans—CH=CH—.

13. 11-deoxy-11α-hydroxymethyl-19-hydroxy-19-methyl-PGF$_2$β, amide, a compound according to claim 12.

14. A compound according to claim 3, wherein W is oxo.

15. A compound according to claim 14, wherein R$_2$ is hydroxyl and X is trans—CH=CH—.

16. 19-hydroxy-19-methyl-PGE$_2$, amide, a compound according to claim 15.

17. A compound according to claim 14, wherein R$_2$ is hydroxymethyl and X is trans—CH=CH—.

18. 11-deoxy-11α-hydroxymethyl-19-hydroxy-19-methyl-PGE$_2$, amide, a compound according to claim 17.

19. A compound according to claim 3, wherein W is methylene.

20. A compound according to claim 19, wherein R$_2$ is hydroxyl and X is trans—CH=CH—.

21. 9-deoxo-9-methylene-19-hydroxy-19-methyl-PGE$_2$, amide, a compound according to claim 20.

22. A compound according to claim 19, wherein R$_2$ is hydrogen and X is trans—CH=CH—.

23. 9-deoxo-9-methylene-11-deoxy-19-hydroxy-19-methyl-PGE$_2$, amide, a compound according to claim 22.

24. A compound according to claim 19, wherein R$_2$ is hydroxymethyl and X is trans—CH=CH—.

25. 9-deoxo-9-methylene-11-deoxy-11α-hydroxymethyl-19-hydroxy-19-methyl-PGE$_2$, amide, a compound according to claim 24.

26. A compound according to claim 2, wherein D is cis—CH$_2$—CH=CH—CH$_2$—CH$_2$—.

27. A compound according to claim 26, wherein W is α-OH:β-H.

28. A compound according to claim 27, wherein R$_2$ is hydroxyl.

29. A compound according to claim 28, wherein X is trans—CH=CH—.

30. 4,5-didehydro-19-hydroxy-19-methyl-PGF$_1$α, amide, a compound according to claim 29.

31. 4,5-didehydro-19-hydroxy-19-methyl-15(S)-15-methyl-PGF$_1$α, amide, a compound according to claim 29.

32. A compound according to claim 28, wherein X is —C≡C—.

33. 4,5,13,14-tetradehydro-19-hydroxy-19-methyl-PGF$_1$α, amide, a compound according to claim 32.

34. 4,5,13,14-tetradehydro-19-hydroxy-19-methyl-16,16-difluoro-PGF$_1$α, amide, a compound according to claim 32.

35. A compound according to claim 27, wherein R$_2$ is hydroxymethyl.

36. A compound according to claim 35, wherein X is trans—CH=CH—.

37. 4,5-dideoxy-19-hydroxy-19-methyl-11-deoxy-11α-hydroxymethyl-PGF$_1$α, amide, a compound according to claim 36.

38. 4,5-dideoxy-19-hydroxy-19-methyl-11-deoxy-11α-hydroxymethyl-15(S)-15-methyl-PGF$_1$α, amide, a compound according to claim 36.

39. A compound according to claim 35, wherein X is —C≡C—.

40. 4,5,13,14-tetradehydro-19-hydroxy-19-methyl-11-deoxy-11α-hydroxymethyl-PGF$_1$α, amide, a compound according to claim 39.

41. 4,5,13,14-tetradehydro-19-hydroxy-19-methyl-11-deoxy-11α-hydroxymethyl-16,16-difluoro-PGF$_1$α, amide, a compound according to claim 39.

42. A compound according to claim 26, wherein W is β-OH:α-H.

43. A compound according to claim 42, wherein R$_2$ is hydroxyl.

44. A compound according to claim 43, wherein X is trans—CH=CH—.

45. 4,5-didehydro-19-hydroxy-19-methyl-PGF$_1$β, amide, a compound according to claim 44.

46. 4,5-didehydro-19-hydroxy-19-methyl-15(S)-15-methyl-PGF$_1$β, amide, a compound according to claim 44.

47. A compound according to claim 43, wherein X is —C≡C—.

48. 4,5,13,14-tetradehydro-19-hydroxy-19-methyl-PGF$_1$β, amide, a compound according to claim 47.

49. 4,5,13,14-tetradehydro-19-hydroxy-19-methyl-16,16-difluoro-PGF$_1$β, amide, a compound according to claim 47.

50. A compound according to claim 42, wherein R$_2$ is hydroxymethyl.

51. A compound according to claim 50, wherein X is trans—CH=CH—.

52. 4,5-didehydro-19-hydroxy-19-methyl-11-deoxy-11α-hydroxymethyl-PGF$_1$β, amide, a compound according to claim 51.

53. 4,5-didehydro-19-hydroxy-19-methyl-11-deoxy-11α-hydroxymethyl-15(S)-15-methyl-PGF$_1$β, amide, a compound according to claim 51.

54. A compound according to claim 50, wherein X is —C≡C—.

55. 4,5,13,14-tetradehydro-19-hydroxy-19-methyl-11-deoxy-11α-hydroxymethyl-PGF$_1$β, amide, a compound according to claim 54.

56. 4,5,13,14-tetradehydro-19-hydroxy-19-methyl-11-deoxy-11α-hydroxymethyl-16,16-difluoro-PGF$_1$β, amide, a compound according to claim 54.

57. A compound according to claim 26, wherein W is oxo.

58. A compound according to claim 57, wherein X is trans—CH=CH—.

59. A compound according to claim 58, wherein X is trans—CH=CH—.

60. 4,5-didehydro-19-hydroxy-19-methyl-PGE$_1$, amide, a compound according to claim 59.

61. 4,5-didehydro-19-hydroxy-19-methyl-15(S)-15-methyl-PGE$_1$, amide, a compound according to claim 59.

62. A compound according to claim 58, wherein X is —C≡C—.

63. 4,5,13,14-tetradehydro-19-hydroxy-19-methyl-PGE$_1$, amide, a compound according to claim 62.

64. 4,5,13,14-tetradehydro-19-hydroxy-19-methyl-16,16-difluoro-PGE$_1$, amide, a compound according to claim 62.

65. A compound according to claim 57, wherein R$_2$ is hydroxymethyl.

66. A compound according to claim 65, wherein X is trans—CH=CH—.

67. 4,5-didehydro-19-hydroxy-19-methyl-11-deoxy-11α-hydroxymethyl-PGE$_1$, amide, a compound according to claim 66.

68. 4,5-didehydro-19-hydroxy-19-methyl-11-deoxy-11α-hydroxymethyl-15(S)-15-methyl-PGE$_1$, amide, a compound according to claim 66.

69. A compound according to claim 65, wherein X is —C≡C—.

70. 4,5,13,14-tetradehydro-19-hydroxy-19-methyl-11-deoxy-11α-hydroxymethyl-PGE$_1$, amide, a compound according to claim 69.

71. 4,5,13,14-tetradehydro-19-hydroxy-19-methyl-11-deoxy-11α-hydroxymethyl-16,16-difluoro-PGE$_1$, amide, a compound according to claim 69.

72. A compound according to claim 26, wherein W is methylene.

73. A compound according to claim 72, wherein R$_2$ is hydroxyl.

74. A compound according to claim 73, wherein X is trans—CH=CH—.

75. 4,5-didehydro-19-hydroxy-19-methyl-9-deoxo-9-methylene-PGE$_1$, amide, a compound according to claim 74.

76. 4,5-didehydro-19-hydroxy-19-methyl-9-deoxo-9-methylene-15(S)-15-methyl-PGE$_1$, amide, a compound according to claim 74.

77. A compound according to claim 73, wherein X is —C≡C—.

78. 4,5,13,14-tetradehydro-19-hydroxy-19-methyl-9-deoxo-9-methylene-PGE$_1$, amide, a compound according to claim 77.

79. 4,5,13,14-tetradehydro-19-hydroxy-19-methyl-9-deoxo-9-methylene-16,16-difluoro-PGE$_1$, amide, a compound according to claim 77.

80. A compound according to claim 72, wherein R$_2$ is hydroxymethyl.

81. A compound according to claim 80, wherein X is trans—CH=CH—.

82. 4,5-didehydro-19-hydroxy-19-methyl-9-deoxo-9-methylene-11-deoxy-11α-hydroxymethyl-PGE$_1$, amide, a compound according to claim 81.

83. 4,5-didehydro-19-hydroxy-19-methyl-9-deoxo-9-methylene-11-deoxy-11α-hydroxymethyl-15(S)-15-methyl-PGE$_1$, amide, a compound according to claim 81.

84. A compound according to claim 80, wherein X is —C≡C—.

85. 4,5,13,14-tetradehydro-19-hydroxy-19-methyl-9-deoxo-9-methylene-11-deoxy-11α-hydroxymethyl-PGE$_1$, amide, a compound according to claim 84.

86. 4,5,13,14-tetradehydro-19-hydroxy-19-methyl-9-deoxo-9-methylene-11-deoxy-11α-hydroxymethyl-16,16-difluoro-PGE$_1$, amide, a compound according to claim 84.

87. A compound according to claim 1, wherein D is trans—(CH$_2$)$_3$—CH=CH—.

88. A compound according to claim 87, wherein W is α-OH:β-H.

89. A compound according to claim 88, wherein R$_2$ is hydroxyl and X is trans—CH=CH—.

90. 2,3-didehydro-19-hydroxy-19-methyl-PGF$_1$α, amide, a compound according to claim 89.

91. 2,3-didehydro-19-hydroxy-19-methyl-16,16-difluoro-PGF$_1$α, amide, a compound according to claim 89.

92. 2,3-didehydro-19-hydroxy-19-methyl-15(S)-15-methyl-PGF$_1$α, amide, a compound according to claim 89.

93. A compound according to claim 88, wherein $R_2$ is hydroxymethyl and X is trans—CH=CH—.

94. 2,3-didehydro-19-hydroxy-19-methyl-11-deoxy-11α-hydroxymethyl-PGF$_{1}$α, amide, a compound according to claim 93.

95. 2,3-didehydro-19-hydroxy-19-methyl-11-deoxy-11α-hydroxymethyl-16,16-difluoro-PGF$_{1}$α, amide, a compound according to claim 93.

96. 2,3-didehydro-19-hydroxy-19-methyl-11-deoxy-11α-hydroxymethyl-15(S)-15-methyl-PGF$_{1}$α, amide, a compound according to claim 93.

97. A compound according to claim 87, wherein W is β-OH:α-H.

98. A compound according to claim 97, wherein $R_2$ is hydroxyl and X is trans—CH=CH—.

99. 2,3-didehydro-19-hydroxy-19-methyl-PGF$_{1}$β, amide, a compound according to claim 98.

100. 2,3-didehydro-19-hydroxy-19-methyl-16,16-difluoro-PGF$_{1}$β, amide, a compound according to claim 98.

101. 2,3-didehydro-19-hydroxy-19-methyl-15(S)-15-methyl-PGF$_{1}$β, amide, a compound according to claim 98.

102. A compound according to claim 97, wherein $R_2$ is hydroxymethyl and X is trans—CH—CH—.

103. 2,3-didehydro-19-hydroxy-19-methyl-11-deoxy-11α-hydroxymethyl-PGF$_{1}$β, amide, a compound according to claim 102.

104. 2,3-didehydro-19-hydroxy-19-methyl-11-deoxy-11α-hydroxymethyl-16,16-difluoro-PGF$_{1}$β, amide, a compound according to claim 102.

105. 2,3-didehydro-19-hydroxy-19-methyl-11-deoxy-11α-hydroxymethyl-15(S)-15-methyl-PGF$_{1}$β, amide, a compound according to claim 102.

106. A compound according to claim 87, wherein W is oxo.

107. A compound according to claim 106, wherein $R_2$ is hydroxyl and X is trans—CH=H—.

108. 2,3-didehydro-19-hydroxy-19-methyl-PGE$_1$, amide, a compound according to claim 107.

109. 2,3-didehydro-19-hydroxy-19-methyl-16,16-difluoro-PGE$_1$, amide, a compound according to claim 107.

110. 2,3-didehydro-19-hydroxy-19-methyl-15(S)-15-methyl-PGE$_1$, amide, a compound according to claim 107.

111. A compound according to claim 106, wherein $R_2$ is hydroxymethyl and X is trans—CH=CH—.

112. 2,3-didehydro-19-hydroxy-19-methyl-11-deoxy-11α-hydroxymethyl-PGE$_1$, amide, a compound according to claim 111.

113. 2,3-didehydro-19-hydroxy-19-methyl-11-deoxy-11α-hydroxymethyl-16,16-difluoro-PGE$_1$, amide, a compound according to claim 111.

114. 2,3-didehydro-19-hydroxy-19-methyl-11-deoxy-11α-hydroxymethyl-15(S)-15-methyl-PGE$_1$, amide, a compound according to claim 111.

115. A compound according to claim 57, wherein W is methylene.

116. A compound according to claim 115, wherein $R_2$ is hydroxyl and X is trans—CH=CH—.

117. 2,3-didehydro-19-hydroxy-19-methyl-9-deoxo-9-methylene-PGE$_1$, amide, a compound according to claim 116.

118. 2,3-didehydro-19-hydroxy-19-methyl-9-deoxo-9-methylene-16,16-difluoro-PGE$_1$, amide, a compound according to claim 116.

119. 2,3-didehydro-19-hydroxy-19-methyl-9-deoxo-9-methylene-15(S)-15-methyl-PGE$_1$, amide, a compound according to claim 116.

120. A compound according to claim 115, wherein $R_2$ is hydroxymethyl and X is trans—CH=CH—.

121. 2,3-didehydro-19-hydroxy-19-methyl-9-deoxo-9-methylene-11-deoxy-11α-hydroxymethyl-PGE$_1$, amide, a compound according to claim 120.

122. 2,3-didehydro-19-hydroxy-19-methyl-9-deoxo-9-methylene-11-deoxy-11α-hydroxymethyl-16,16-difluoro-PGE$_1$, amide, a compound according to claim 120.

123. 2,3-didehydro-19-hydroxy-19-methyl-9-deoxo-9-methylene-11-deoxy-11α-hydroxymethyl-15(S)-15-methyl-PGE$_1$, amide, a compound according to claim 120.

124. A compound according to claim 2, wherein D is —(CH$_2$)$_3$—(CH$_2$)$_g$—CH$_2$—, wherein g is zero, one, two, or three.

125. A compound according to claim 124, wherein g is one.

126. A compound according to claim 125, wherein W is α-OH:β-H.

127. A compound according to claim 126, wherein $R_2$ is hydroxyl.

128. A compound according to claim 127, wherein X is trans—CH=CH—.

129. 19-hydroxy-19-methyl-PGF$_{1}$α, amide, a compound according to claim 128.

130. 16,16-dimethyl-19-hydroxy-19-methyl-PGF$_{1}$α, amide, a compound according to claim 128,.

131. 16,16-difluoro-19-hydroxy-19-methyl-PGF$_{1}$α, amide, a compound according to claim 128.

132. A compound according to claim 127, wherein X is —CH$_2$CH$_2$—.

133. 13,14-dihydro-19-hydroxy-19-methyl-PGF$_{1}$α, amide, a compound according to claim 132.

134. A compound according to claim 126, wherein $R_2$ is hydroxymethyl.

135. A compound according to claim 134, wherein X is trans—CH=CH—.

136. 11-deoxy-11α-hydroxymethyl-19-hydroxy-19-methyl-PGF$_{1}$α, amide, a compound according to claim 135.

137. 11-deoxy-11α-hydroxymethyl-16,16-dimethyl-19-hydroxy-19-methyl-PGF$_{1}$α, amide, a compound according to claim 135.

138. 11-deoxy-11α-hydroxymethyl-16,16-difluoro-19-hydroxy-19-methyl-PGF$_{1}$α, amide, a compound according to claim 135.

139. A compound according to claim 134, wherein X is —CH$_2$CH$_2$—.

140. 11-deoxy-11α-hydroxymethyl-13,14-dihydro-19-hydroxy-19-methyl-PGF$_{1}$α, amide, a compound according to claim 139.

141. A compound according to claim 125, wherein W is β-OH:α-H.

142. A compound according to claim 141, wherein $R_2$ is hydroxyl.

143. A compound according to claim 142, wherein X is trans—CH=CH—.

144. 19-hydroxy-19-methyl-PGF$_{1}$β, amide, a compound according to claim 143.

145. 16,16-dimethyl-19-hydroxy-19-methyl-PGF$_{1}$β, amide, a compound according to claim 143.

146. 16,16-difluoro-19-hydroxyl-19-methyl-PGF$_{1}$β, amide, a compound according to claim 143.

147. A compound according to claim 142, whrein X is —CH$_2$CH$_2$—.

148. 13,14-dihydro-19-hydroxy-19-methyl-PGF$_2\beta$, amide, a compound according to claim 147.

149. A compound according to claim 125, wherein W is oxo.

150. A compound according to claim 149, wherein R$_2$ is hydroxyl.

151. A compound according to claim 150, wherein X is trans—CH═CH—.

152. 19-hydroxy-19-methyl-PGE$_1$, amide, a compound according to claim 151.

153. 16,16-dimethyl-19-hydroxy-19-methyl-PGE$_1$, amide, a compound according to claim 151.

154. 16,16,difluoro-19-hydroxy-19-methyl-PGE$_1$, amide, a compound according to claim 151.

155. A compound according to claim 150, wherein X is —CH$_2$CH$_2$—.

156. 13,14-dihydro-19-hydroxy-19-methyl-PGE$_1$, amide, a compound according to claim 155.

157. A compound according to claim 149, wherein R$_2$ is hydroxymethyl.

158. A compound according to claim 157, wherein X is trans—CH═CH—.

159. 11-deoxy-11α-hydroxymethyl-19-hydroxy-19-methyl-PGE$_1$, amide, a compound according to claim 158.

160. 11-deoxy-11α-hydroxymethyl-16,16-dimethyl-19-hydroxy-19-methyl-PGE$_1$, amide, a compound according to claim 158.

161. 11-deoxy-11α-hydroxymethyl-16,16-difluoro-19-hydroxy-19-methyl-PGE$_1$, amide, a compound according to claim 158.

162. A compound according to claim 157, wherein X is —CH$_2$CH$_2$—.

163. 11-deoxy-11α-hydroxymethyl-13,14-dihydro-19-hydroxy-PGE$_1$, amide, a compound according to claim 162.

164. A compound according to claim 125, wherein W is methylene.

165. A compound according to claim 164, wherein R$_2$ is hydroxyl.

166. A compound according to claim 165, wherein X is trans—CH═CH—.

167. 9-deoxo-9-methylene-19-hydroxy-19-methyl-PGE$_1$, amide, a compound according to claim 166.

168. 9-deoxo-9-methylene-16,16-dimethyl-19-hydroxy-19-methyl-PGE$_1$, amide, a compound according to claim 166.

169. 9-deoxo-9-methylene-16,16-difluoro-19-hydroxy-19-methyl-PGE$_1$, amide, a compound according to claim 167.

170. A compound according to claim 165, wherein X is —CH$_2$CH$_2$—.

171. 9-deoxo-9-methylene-13,14-dihydro-19-hydroxy-19-methyl-PGE$_1$, amide, a compound according to claim 170.

172. A compound according to claim 164, wherein R$_2$ is hydroxymethyl.

173. A compound according to claim 172, wherein X is trans—CH═CH—.

174. 9-deoxo-9-methylene-11-deoxy-11α-hydroxymethyl-19-hydroxy-19-methyl-PGE$_1$, amide, a compound according to claim 173.

175. 9-deoxo-9-methylene-11-deoxy-11α-hydroxymethyl-16,16-dimethyl-19-hydroxy-19-methyl-PGE$_1$, amide, a compound according to claim 173.

176. 9-deoxo-9-methylene-11-deoxy-11α-hydroxymethyl-16,16-difluoro-19-hydroxy-19-methyl-PGE$_1$, amide, a compound according to claim 173.

177. A compound according to claim 172, wherein X is —CH$_2$CH$_2$—.

178. 9-deoxo-9-methylene-11-deoxy-11α-hydroxymethyl-13,14-dihydro-19-hydroxy-19-methyl-PGE$_1$, amide, a compound according to claim 177.

* * * * *

UNITED STATES PATENT OFFICE
CERTIFICATE OF CORRECTION

Patent No. 4,281,191          Dated       28 July 1981

Inventor(s)   John C. Sih

It is certified that error appears in the above-identified patent and that said Letters Patent are hereby corrected as shown below:

Column 1, lines 32-38, and Column 5, lines 17-24, that portion of the formula reading

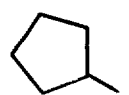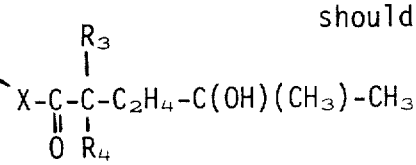   should read   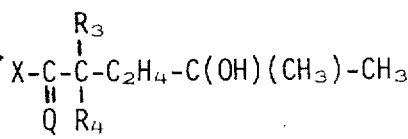

Column 9, line 25, "trans-CH-CH-" should read -- trans-CH=CH- --; line 39, "trans-CH=H-" should read -- trans-CH=CH- --; line 59, "according to claim 57" should read -- according to claim 87 --;
Column 12, line 14, "according to claim 167" should read -- according to claim 166 --.

Signed and Sealed this

*Tenth* Day of *November 1981*

[SEAL]

*Attest:*

*Attesting Officer*

GERALD J. MOSSINGHOFF

*Commissioner of Patents and Trademarks*